United States Patent [19]

Mulhollan et al.

[11] Patent Number: 4,602,635
[45] Date of Patent: Jul. 29, 1986

[54] REMOTE SURGICAL KNOT TIER AND METHOD OF USE

[76] Inventors: James S. Mulhollan, 3410 Foxcroft Rd., Little Rock, Ark. 72207; Lionel Starr, 8806 Patricia Lynn, Sherwood, Ark. 72116

[21] Appl. No.: 551,038

[22] Filed: Nov. 14, 1983

[51] Int. Cl.⁴ .............................................. A61B 17/04
[52] U.S. Cl. ................................. 128/334 R; 128/325; 128/326; 128/334 C; 128/340
[58] Field of Search ............... 128/334 R, 334 C, 325, 128/326, 340, 303 R

[56] References Cited

U.S. PATENT DOCUMENTS 4,177,813 12/1979 Miller et al. ..................... 128/326

Primary Examiner—Lucille M. Phynes
Attorney, Agent, or Firm—Hill, Van Santen, Steadman & Simpson

[57] ABSTRACT

A remote surgical knot tier and method for its use is provided which can hold, push and place loops forming a knot in suture material from a manipulation area into a remote site in the body of a human being or an animal through a puncture wound or other small opening.

9 Claims, 7 Drawing Figures

Viewing Screen — 26

REMOTE SURGICAL KNOT TIER AND METHOD OF USE

BACKGROUND OF THE INVENTION

1. Field of the Invention

This invention relates to surgical instruments and more particularly to a method and device for tying, holding and placing knots in suture material within a body of tissue or cartilage such as the body of a human being or of an animal.

2. Description of the Prior Art

Many surgical procedures are currently being performed where it is necessary to make a large opening to expose the area of, for instance, a human body that requires surgical repair. This is true even though there are instruments available which allow the viewing of certain areas which have limited accessibility. For example, arthroscopes are available to permit viewing of a human knee joint through a puncture wound without exposing the entire joint of the knee by cutting through the skin in that area.

These viewing instruments can be used to detect, among other things, surgically repairable tears within the cartilage of the knee. Shaving instruments exist which allow parts of the damaged cartilage to be shaven off and removed from the knee joint through a cannula or tube without requiring that the knee be opened. However, prior to this time it has been necessary to open the knee to sew a tear in the cartilage.

When an area of the body is cut into to expose an interior portion thereof, that process involves some morbidity which increases as more muscle layers, ligaments and other tissues are cut and separated. This morbidity, or time and discomfort associated with recovery and chance of complications, would be greatly reduced if the required surgery were performed without making a large incision, cutting and separating various tissues, and exposing a large portion of the interior of the body.

SUMMARY OF THE INVENTION

The invention provides for a method and device for performing surgical repair requiring stitches on areas of the interior of a body having limited access. This can be done percutaneously, or through a puncture wound in the skin, without requiring a large incision for exposing the interior of the body. Also the present device is beneficial when a large incision is made, but the area where the stitches are to be placed is nevertheless inaccessible. The device of the present invention comprises a remote surgical knot tier which is small enough to be inserted through a cannula. The device is operable to hold and place a knot in suture material in a cavity in the body which is relatively inaccessible by means of carrying or pushing the loop of a knot along the suture material to the point where the stitch is to be set and then holding it while the knot is tightened.

Thus, the present invention provides the advantage of being able to make repairs requiring stitches within the interior of a body in a relatively inaccessible area either through a puncture wound without making a large incision or through a large incision partially exposing an inaccessible area.

BRIEF DESCRITION OF THE DRAWINGS

DESCRIPTION OF THE PREFERRED EMBODIMENTS

Figure 1:
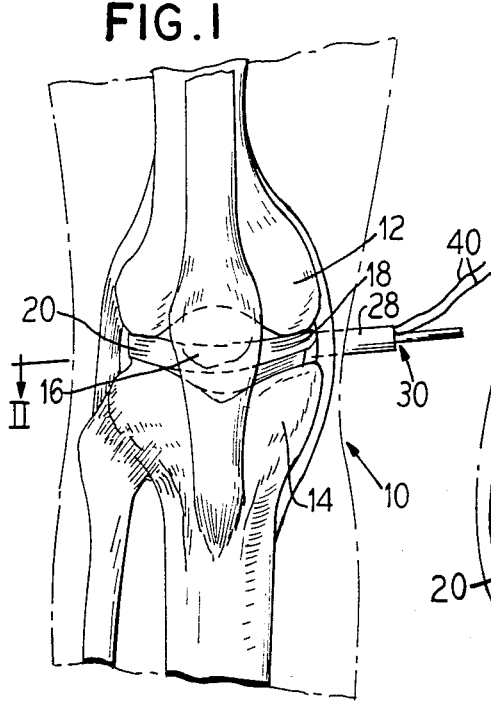
FIG. 1 is a front view of the environment of a human knee showing the joint structure in full lines and the outline of a leg in phantom and showing the remote knot tier device in place.
Figure 2:
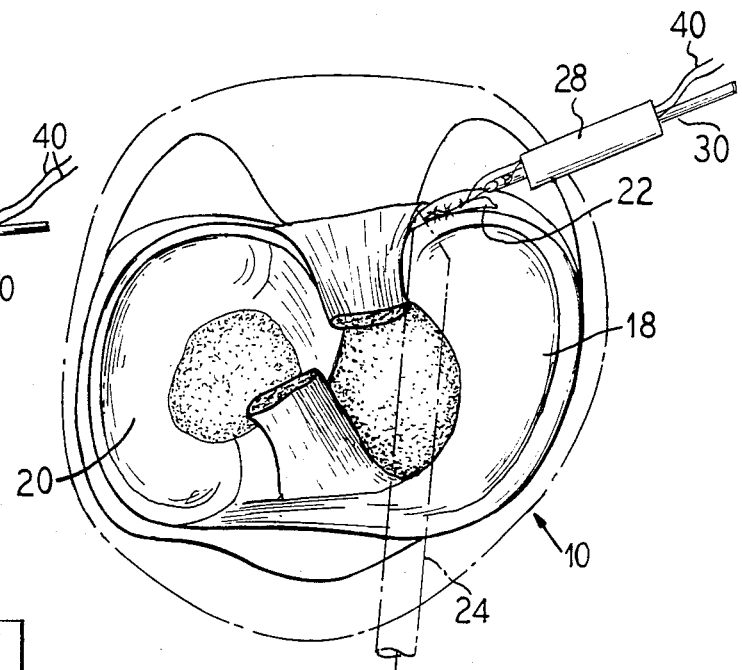
FIG. 2 is a top sectional view through the knee showing the placement of the remote knot tier device in operation, taken generally along the line II—II of FIG. 1.

Although the principles of the present invention are applicable to any device suitable in surgical procedures whether performed on humans or animals, a particular utility is effected in human knee surgery where the problems of surgery are particularly acute. Accordingly, as an illustrative exemplification of my invention in FIG. 1 there is shown a human knee joint generally at 10 which provides an environment in which the present invention is especially useful. Within the knee joint 10 there is shown the femur bone 12, the tibia bone 14, the patella or knee cap 16 and the medial meniscus 18 and lateral meniscus 20. The menisci 18, 20 are cartilage structures in contact with both the femur 12 and tibia 14. As seen in FIG. 2, the menisci are crescent shaped with a central open area. Certain injuries to the knee cause tears to the menisci such as that shown at 22 in FIG. 2.

Arthroscopes are available which have a light and optics probe, as shown at 24, which can be inserted through a puncture wound for viewing the interior portion of the knee joint 10 through a viewing lens or screen shown schematically at 26 (FIG. 2). The arthroscope permits the physician or surgeon to see the tear 22 without surgically opening the knee to expose that portion of the joint.

A hollow cannula or access tube 28 can be inserted through the skin around the knee joint to a position proximate to the tear 22 in the meniscus 18. Various instruments can be inserted through these cannula 28 to perform various surgical tasks. The present invention provides for an instrument which can be inserted through these cannula 28 to assist in tying a stitch in suture material sewn through the meniscus. This allows the tear 22 to be sewn shut to assist in the healing process without opening the knee to expose this portion of the knee joint. Such a procedure is greatly advantageous over previous methods of knee surgery in that the repair can be performed with greater accuracy, the patient expriences less pain, has a smaller scar, and a shorter hospital stay. Rehabilitation of the knee joint after surgery is not required anywhere near the degree to which it has heretofore been required. Similar results can be obtained for surgery on other parts of the human body or on animals.

Figure 3:
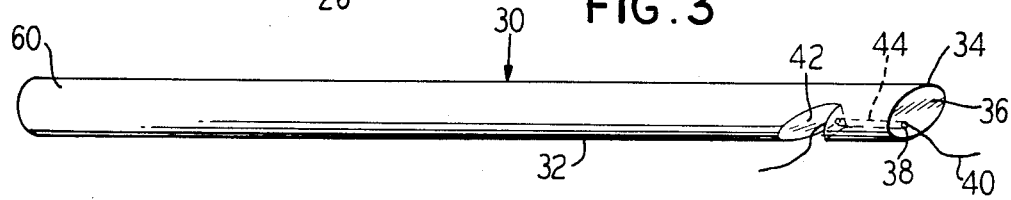
FIG. 3 is a side elevational view of the knot tier device with suture material inserted through the tip.

A remote surgical knot tier 30 is shown in detail in FIG. 3 and is comprised of a cylindrical rod member 32 having an angularly cut end 34 which may be non-perpendicular to the length of the rod member 32 to increase the area of a flat face 36 at the end of the rod member 32. The cylindrical rod member 32 is of a diameter sufficiently lesser than the inner diameter of the cannula bore to afford a clearance allowing it to move loosely in the cannula 28. A typical diameter for the cylindrical rod member would be about 25 mm. The angled end 34 of the rod member 32 having the flat face area 36 also has a small hole 38 therein. The hole 38 is large enough to allow surgical suture material 40 to pass therethrough.

Positioned a short distance behind the angled face 36 of the rod member 32 is a notch 42. The hole 38 in the face 36 extends into the rod member 32 and forms a tunnel or passage 44 which communicates with the notch 42. Thus, the suture material 40 is carried by the rod member 32 through the tunnel 44 in the tip of the rod.

Figure 4:
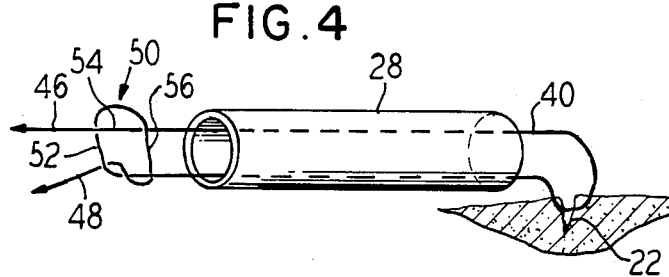
FIG. 4 is a schematic view of the suture material extending through the cannula and through injured tissue and with a first knot therein.
Figure 5:
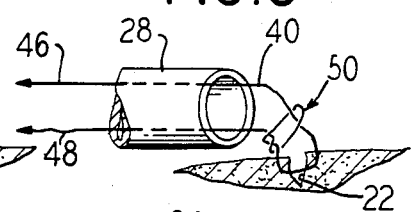
FIG. 5 is a partial schematic view of the first knot positioned at the point where the stitch is to be set in the injured tissue.
Figure 6:
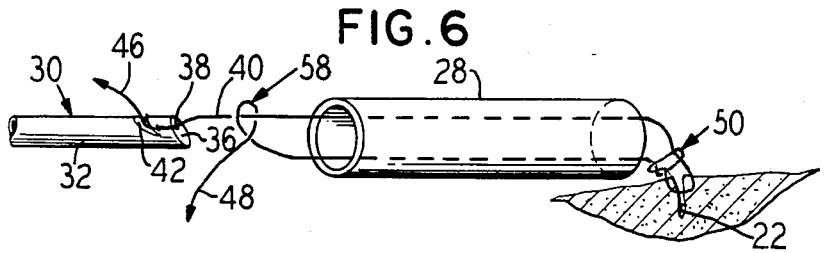
FIG. 6 is a schematic view of the device showing a second loop or any subsequent loop placed in the suture material.

The method of tying a surgical knot is shown in FIGS. 4 5 and 6. FIG. 4 schematically shows the suture material 40 passing through the tear 22 in the tissue at a remote, relatively inaccessible site and the entire length of the suture material 40 extending throught the hollow cannula or access tube 28 to an area of manipulation, such that both ends 46, 48 of the suture material are available for manipulation. The cannula 28 is not necessary, espeically when there is a large incision, however, use of a cannula simplifies the procedure by providing a clear passage for the suture material 40 and the remote knot tier device 30.

A first knot 50 is placed by passing suture end 48 under the other length of suture and back around behind itself, then through the loop so created. Thus, suture segment 52 is under segment 54, segment 54 is under segment 56 and segment 56 is under segment 52. Suture 48 then passes over segment 52 below 54 creating a simple knot 50 illustrated by FIG. 4. End 48 is pulled and the knot 50 is tightened. By pulling on end 46, and releasing tension on end 48, the knot 50 is caused to be pulled through the cannula 28 to the point where the stitch has been placed at the tear 22 in the tissue, as is shown in FIG. 5. When the knot 50 is set in place at the tear 22, the suture material 40 wil be held fixed in place and additional loops needed to complete the knot will not be able to be pulled into place as the first one was. Loops of a knot usually require either a broad diameter to set, from two remote points, or a "finger" to apply at the knot itself. Neither the large diameter nor accessibility for a human finger is available when surgery is being performed in a relatively inaccessible remote location, so the remote knot tier device 30 is utilized to set additional loops.

Figure 7:
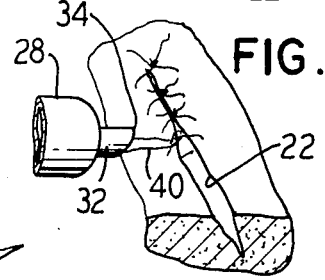
FIG. 7 is a perspective schematic view of the device showing the tying of several stitches in the injured tissue.

As is shown in FIG. 6, the end 46 of the suture material 40 is passed through the tunnel 44 and out through the notch 42. Tension on end 46 holds simple knot 50 tight at the tear location. A second loop 58 is placed in the suture material 40 by manipulating the end 48. Tension is held on end 46 and end 48 is held loosely while the rod member 32 is advanced through the cannula 28, pushing loop 58 toward the first knot 50. The hole 38 in the face 36 is offset from the center to permit a large face area to be used to push the loop 58 along the suture material 40. FIGS. 2 and 7 show the angled end 34 adjacent the tear 22 in the injured tissue, thus setting the loop in place. When the flat face 36 abuts the tear, tension on end 48 will tighten the loop and the face 36 of the rod member 32 acts as a finger to hold the loop so the loop can be tightened and set as part of the knot.

The rod member 32 is of a sufficient length so that a free end 60 thereof can be held and manipuated while the face 36 is holding the loop against the tear 22. The rod member is withdrawn from the cannula 28 after the loop is tightened and additional loops can be passed down to the knot in similar fashion such that a secure knot will be tied. Excess suture material can be cut off and removed by other instruments known in the art. Additional stitches can be placed in the injured tissue and knots tied, as seen in FIG. 7, by repeating the above steps until the active cut or tear has been securely sewn.

Although various modifications may be suggested by those skilled in the art, it should be understood that we wish to cover within the scope of the patent warranted hereon all such modifications as reasonably and properly come within the scope of our contribution to the art.

I claim as our invention:

1. A remote surgical knot tier comprising:
   means for being guided along a length of suture material,
   means for pushing a loop of suture material along said length, and
   means for holding said loop such that said loop can be tightened.

2. The device of claim 1 wherein said means for being guided along said suture material comprises a tunnel through said knot tier.

3. The device of claim 2 wherein said means for pushing said loop of suture material comprises a flat face with which said tunnel communicates at an opening.

4. A remote surgical knot tier which comprises:
   a rod member having
   a flat end,
   a tunnel therethrough communicating at an opening with said flat end,
   said tunnel sized to receive surgical suture material, and
   said flat end having a large surface area in comparison with said tunnel opening.

5. The remote knot tier of claim 4 including a notch in the side of said rod member communicating with a second end of said tunnel.

6. The device of claim 4 wherein said flat end is at a non-perpendicular angle to the length of said rod member.

7. The device of claim 4 wherein said tunnel communicates with said flat end at a point offset from the center of said flat face.

8. The method of tying a surgical knot at a remote site by using a remote knot tier comprising a rod member having a flat end and a tunnel therethrough communicating with said flat end, where suture material has been inserted through injured tissue at said remote site and two ends of the suture material extend to a manipulation area comprising the steps:
   (1) placing a first knot in the suture material by manipulating said first end with respect to said second end in the manipulation area,
   (2) pulling said first end of said suture material until said knot is tightened,
   (3) pulling said second end of said suture material until said knot is pulled to said remote site,
   (4) threading said second end of said suture material through said tunnel in said remote knot tier, (5) placing an additional loop in the suture material by manipulating said first end in front of said knot tier,
(6) holding said second end taut while pushing said loop to said remote site with said flat end of said knot tier,
(7) pulling said first end of said suture material while said flat end holds said loop, until said loop is tightened,
(8) repeating steps 5–7 until a secure knot is tied.

9. The device of claim 3, wherein said flat face has a large surface area in comparison with an area of said tunnel opening.

* * * * *